United States Patent
Mamedov et al.

(10) Patent No.: US 7,355,088 B2
(45) Date of Patent: Apr. 8, 2008

(54) PROCESS FOR PRODUCING BENZENE, ETHYLENE AND SYNTHESIS GAS

(75) Inventors: Agaddin Mamedov, Riyadh (SA); Tony Joseph, Riyadh (SA); Akram Al-Alwan, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 445 days.

(21) Appl. No.: 10/871,212

(22) Filed: Jun. 18, 2004

(65) Prior Publication Data

US 2004/0267079 A1 Dec. 30, 2004

(30) Foreign Application Priority Data

Jun. 20, 2003 (EP) .................................. 03013408

(51) Int. Cl.
C07C 2/00 (2006.01)
C07C 6/00 (2006.01)

(52) U.S. Cl. ...................... 585/943; 585/417; 585/418

(58) Field of Classification Search ................ 208/133, 208/134, 135, 136; 585/24, 400, 407, 412, 585/415, 417, 418, 420, 421, 924, 925, 943
See application file for complete search history.

(56) References Cited

U.S. PATENT DOCUMENTS 4,239,658 A * 12/1980 Mitchell et al. ............. 502/302
4,507,517 A    3/1985 Devries
4,734,537 A * 3/1988 Devries et al. ............. 585/415

FOREIGN PATENT DOCUMENTS

GB         2148933      1/1985

OTHER PUBLICATIONS

Ohnishi et al., Catalytic Dehydrocondensation of Methane with CO and CO2 toward Benzene and Naphthalene on Mo/HZSM-5 and Fe/Co-Modified Mo/HZSM-5, 182 J. CATAL. 92-103 (1999).*
Tan et al., Methane Aromatization Over 2 wt% Mo/HZSM-5 in the Presence of O2 and NO, 78 CATAL. LETT. 251-258 (2002).*
Columbia Electronic Encyclopedia (2007) available at http://columbia.thefreedictionary.com/p/lanthanide.*
Mamedov A KH, "Heterogeneous-oxidative catalysis by Co2 . . . Properties and reactivity of the oxygen, generated from carbon dioxide", ACS 211th National Meeting, ACS Division of Petroleum Chemistry, Inc., vol. 41, No. 1 58-59, (Feb. 1996), ISSN: 0569-3799, 1996, XP002262607.
Y. Wang et al., "Mn-based binary oxides as catalyst for the conversion of methane to C2 hydrocarbons with carbon dioxide as oxidant", Applied Catalysis A: General, vol. 219, 2001, pp. 183-193, XP002262534 Nlelsevier Science, Amsterdam.
Z. Xiong et al., "Study of W/HZSM-5 based catalysts for dehydroaromatization of CH4 in absence of 02. 1. Peformance of catalysts", Catalysis Letters, vol. 74, 2001, pp. 227-232, XP002262535, Chbaltzer, Scientific Publ, Basel, abstract.
Y. Wang et al., "Carbon dioxide as oxidant for the conversion of methane to ethane and ethylene using modified Ce02 catalysts", Journal of Catalysis, vol. 186, 1999, pp. 160-168, XP002262536, USAcademic Press, Duluth, MN, abstract.
O.V. Krylov et al., "The regularities in the interaction of alkanes with C02 on oxide catalysrs", Catalysis Today, vol. 24, 1995, pp. 371-375, XP002262537, Nlamsterdam.
Li W. Y. et al., "Ni/ZSM-5 catalyst for CH4 reforming with C02", Petroleum Science and Technology V16, N. 5-6, 539-53, ISSN: 1091-6466, 1998, XP002262538.
L. Wang et al., "Selective dehydroaromatization of methane toward benzene on RE/HZSM-5 catalysts and effects of C0/C02 addition", Journal of Catalysis, vol. 190, 2000, pp. 276-283, XP002262539, USAcademic Press, Duluth, MN.
J.H. Lunsford, "Catalytic conversion of methane to more useful chemicals and fuels: a challenge for the 21st century", Catalysis Today, vol. 63, 2000, pp. 165-174, XP002262540 Nlamsterdam.

* cited by examiner

Primary Examiner—Glenn Caldarola
Assistant Examiner—Randy Boyer
(74) Attorney, Agent, or Firm—Jim Wheelington; William J. Spatz

(57) ABSTRACT

Process for producing benzene, ethylene and synthesis gas, comprising the steps of: i) introducing a starting gas flow comprising methane and carbon dioxide into a reactor; ii) oxidizing the methane in the reactor at certain reactor conditions optionally using a first catalytic material and/or and additional oxidant; and iii) removing a product gas flow comprising benzene, ethylene and synthesis gas from the reactor.

29 Claims, No Drawings

PROCESS FOR PRODUCING BENZENE, ETHYLENE AND SYNTHESIS GAS

The present invention relates to a process for producing benzene, ethylene and synthesis gas from methane.

The partial oxidation of methane is of great industrial importance either for the production of synthesis gas or the production of higher hydrocarbons and aromatics, such as benzene.

Nowadays, benzene is often produced by methods comprising the production from catalytic reformate, production from gasoline pyrolysis, production by toluene conversion and production by LPG (Liquified Petroleum Gases) aromatization.

U.S. Pat. No. 4,239,658 discloses that benzene could be detected in a product, if methane was passed over a multi-component catalyst. It was proposed that methane dissociates on metal to Me-CHx and then forms ethane and ethylene and reacts with metallic oxide to form metallic carbide. Finally, the carbide is transformed into benzene. The benzene usually appears in measurable quantities at temperatures above about 1650° F., and in quantities as high as 6-10 weight-% at 2200° F. to 2375° F., or even at higher temperatures. The high temperature and pure methane pyrolysis of U.S. Pat. No. 4,239,658 contributes to the formation of high amounts of coke-polymeric fragments in the form of non-active materials.

Numerous attempts have been made to catalyze these reactions at lower and more feasible temperatures, but such attempts have not been successful.

GB 2,148,933 discloses the conversion of low molecular weight hydrocarbons to higher molecular weight hydrocarbons. The process utilizes a catalyst containing a boron compound, a high reaction temperature of greater than 1000° C. and a high gas space velocity of greater than 3200 $h^{-1}$. The catalyst containing the boron compound provides conversion of the lower molecular weight hydrocarbons of about 19% and maintains this conversion for only about three hours under the temperature and space velocity conditions. The high temperature and the low conversion of methane are responsible for a lower yield of higher molecular weight hydrocarbons.

Methane can be also converted to higher hydrocarbons without using oxidant by thermal coupling. The thermal processes of methane conversion to higher hydrocarbons are well known. One of these processes is the Hüls process (see Gladish H. How Huels Makes Acetylene by DC arc. Pet. Refiner. 1962. 41 (6), 159-165) which has been operated for more than 50 years. The main product produced in these processes was acetylene.

In the BASF thermal methane conversion process (see Forbath T. P. and Gaffney B. J. Acetylene by the BASF process. Pet. Refiner, 1954, 33 (12), 160-165) the endothermic heat for conversion of methane to ethylene was provided by burning part of the methane feed with oxygen.

Methane thermal conversion into higher hydrocarbons in co-feed mode was studied in U.S. Pat. No. 4,507,517 for the reaction mixture $CH_4/O_2$=10:1 in the presence of catalyst $Pt/Cr/Ba/Mg/Al_2O_3$. No aromatics were detected at temperatures below 970 K.

In recent years, investigations are concerned with the non-oxidative dehydrooligomerization of methane in the absence of oxygen using zeolites with molybdenum or other transition ion metals theron. The common formula of such a catalyst is Me-HZSM-5 (Me=metal). The conversion and selectivity of methane using such a catalyst at 700° C. in a pure methane flow was 7.9-8.0% and 72-73.4% respectively, see Bert M. Weskhuysen, Dingjun Wang, Michael P. Rsynek, T. H. Lunsford, T. Catal. 175, 338 (1998). The yield of benzene is about 6%. The catalyst deactivates during the reaction after three hours because of coke accumulation on the surface of the catalyst.

More active catalysts were described by Zhi-Thao Xiong, Hong-Bin Zhang, Guo-Dong Lin and Tin-Long Zeng. Catal. Lett. V. 74, N3-4, 2001. This catalyst has a composition of 3% W-1.5% Li/HZSM-5. The conversion of methane after 105 minutes of methane flow was 21.0% with a selectivity of 61.5%. After 300 minutes of the run, the activity of the catalyst was low: conversion was 17.0%, benzene selectivity was 50%, and the benzene yield was 8.5%.

Further, a catalyst $Zn-W-H_2SO_4/HZSM-5$ was described by Jin-Long Zeng, Zhi-Tao Xiong, Hong-Bin Zhang, Guo-Dong Lin, K. R. Tsai, Catal. Lett. 53 (1998) 119-124, being more active and selective. The yield of benzene was 22%. However, this catalyst deactivates during the reaction because of coke accumulation on the surface and inside of the zeolite channels. The sulfur component of the catalyst is not stable at 700° C. and evaporates during the reaction. For all the Me/HZSM-5 containing catalysts an induction period of about 1.5 to 6 hours is characteristic, after which the catalyst starts to perform until the activity is blocked by formation of coke fragments. After regeneration by air-burning, the performance of the catalyst can be repeated, but the reduction of the catalyst after regeneration for formation of active material takes about 1.5 to 3 hours, and after some cycle operations the performance of the regenerated catalyst is low.

In summary, the method of methane aromatization using zeolites has a lot of disadvantages: very long induction period of the reaction due to a necessary reduction of the metal present on the zeolite; very short time of reaction due to the accumulation of coke fragments in the catalyst channels; a high loss of methane in the form of coke fragments which are to be removed from the catalyst; the formation of high amounts of naphthalene on a generated catalyst; the stable yield of benzene in these methods using methane aromatization on zeolite catalysts is not higher than 8%; a high loss of methane in the form of carbon dioxide in the induction period for reduction of the metal on the zeolite; a formation of coke fragments inside the channels of the zeolite leads to a decrease of catalyst stability and to the destruction of the catalyst size; no sufficient methane conversion.

It is an object of the present invention to provide a process for producing benzene which overcomes the drawbacks of the prior art, especially to provide a process for simultaneously producing benzene, ethylene and synthesis gas with high conversion of methane and with high selectivity and yield of benzene.

This object is achieved by a process for producing benzene, ethylene and synthesis gas, comprising the steps of: i) introducing a starting gas flow comprising methane and carbon dioxide into a reactor, ii) oxidizing the methane in the reactor at certain reactor conditions optionally using a first catalytic material and/or an additional oxidant; and iii) removing a product gas flow comprising benzene, ethylene and synthesis gas from the reactor.

Preferably, the first catalytic material is selected from the group consisting of $Mn(NO_3)_2$, $Si(WO_4)_2$, $KNO_3$, NaOH, and/or $HBO_3$.

Particularly, an inner wall of the reactor is treated with the first catalytic material, which is preferably mixed with $SiO_2$ sol-gel.

It is also possible to use a kind of fixed bed in the reactor for the process of the present invention, wherein the fixed bed may comprise $Al_2O_3$ and/or $SiO_2$.

In one embodiment, the oxidant is introduced together with the starting gas flow or after that starting gas flow has been stopped.

It is preferred that the additional oxidant is oxygen, air, or a mixture of methane and oxygen and/or air.

Still preferred is a process, wherein the concentration of oxidant relative to the starting gas flow amount is not more than 2% (volume-%).

Too high concentrations of oxidant decrease the benzene yield due to deep oxidation of methane to CO and $CO_2$.

More preferred, the process is carried out under isothermal or non-isothermal conditions where the reactor has a temperature profile of from about 600° C. at an outlet of the reactor to about 1500° C. at an inlet of the reactor, preferably from about 700° C. to about 1000° C.

According to a further embodiment of the invention, the starting gas flow is introduced at a temperature of about 965° C. and the product gas flow is discharged from the reactor at a temperature of about 715° C.

Most preferably, the process is carried out in a reactor that is made of quartz, ceramic, alumina alloy, stainless steel or the like. A quartz reactor is preferred, because, for example, in a metallic reactor the benzene yield is low due to the deep decomposition of the methane on the metallic surface.

Still preferred, a second catalytic material is present in the reactor, preferably in an inlet preheat zone of the reactor, preferably on top of the reactor. The second catalytic material is preferably fixed inside the reactor from both sides by quartz wool.

Preferably, the second catalyst is a basic oxide, such as $MnO_2$, $WO_3$, SrO, $La_2O_3$, a mixture of $MnO_2$ with $WO_3$ or a mixture of SrO with $La2O_3$, or any mixture thereof, most preferably $(2-20\%)W—Mn_3O_4/(2-20\%)Sr—La_2O_3$. The disclosure of the latter catalyst composition is to be understood, in that 2 to 20 wt.-% tungsten is inserted into bulk $Mn_3O_4$ or 2 to 20 wt.-% strontium is inserted into bulk $La_2O_3$.

More preferred, the pressure in the reactor is from about 0.1 to about 200 bar.

According to the invention, the contact time of the first catalytic material with the gas flow is from about 0.1 to about 90 seconds.

In one embodiment of the invention, the ratio of methane to carbon dioxide in the starting gas flow is from about 1-99 mol-%:99-1 mol-%, preferably about m40-60 mol-%:70-30 mol-%, and even preferably about 50 mol-%:50 mol-%.

It is preferred that the reactor has an inner diameter of about 2 to 1000 mm.

Still preferred, the length to diameter ratio of the reactor is from about 1 to 200, preferably from about 5 to 100.

Further, it is preferred that the process is conducted continuously or as a batch process.

In a further embodiment, at least a part of the product gas flow is recycled back to the reactor together with the starting gas flow.

In a further embodiment, at least a part of the product gas flow is quenched at the outlet of the reactor to decrease further degradation of products. Quenching could be done by cooler streams such as steam, nitrogen, oil, or with any of the reaction products, such as hydrogen, toluene, heavy aromatics benzene, and the like.

Finally, after removing the product gas flow from the reactor a regeneration step for coke oxidation and burning may be conducted. Regeneration could be done using air and/or methane and/or a mixture of air, ethane and carbon dioxide. Regeneration step outlet gases are substantially carbon dioxide and/or carbon monoxide, hydrogen and/or benzene.

Surprisingly, it was found that the process of the present invention provides a method for producing benzene, ethylene and synthesis gas, the process having a high conversion of methane and high selectivity and yield for benzene. The process additionally produces low amounts of high molecular heavy aromatics, such as toluene, naphthalene, methyl phenylacetylene, antracene, styrene, acetonaphthalene, phenantrene and the like. The process has stable benzene yields for more than two days, and the selectivity for coke fragments is three to four times less than the benzene selectivity. Coke fragments which have been accumulated during the reaction may be converted to synthesis gas by treatment of the reactor with a mixture of methane and air, preferably in a regeneration step, which allows to produce synthesis gas with a ratio of carbon monoxide to hydrogen of about 1:3 at a methane conversion of 35%. The use of carbon dioxide in the process of the present invention allows to oxidize the coke fragments accumulated during the reaction, particularly with carbon dioxide, and carbon dioxide is a mild oxidant and changes the equilibrium and increases the methane conversion. Carbon dioxide as a dilutant decreases the partial pressure of methane and decreases the coke formation.

A low partial pressure of methane avoids the formation of carbon. A dilution with carbon dioxide allows to realize a high methane conversion. Further, the presence of carbon dioxide in a mixture with methane provides the formation of active coke fragments and decreases the formation of graphitic forms of coke. As may be further illustrated below, a dilution with carbon dioxide decreases the concentration of heavy aromatics, such as toluene, naphthalene, acetonaphthalene, phenantrene and the coke formation reactions. Carbon dioxide reacts with coke and hydrogen to produce simultaneously the synthesis gas, which is important for methanol synthesis.

Carbon dioxide as an oxidant participates first in the oxidation of coke fragments and then contributes to the formation of oxidized surfaces after removing the coke fragments. It is assumed that the present process of methane conversion with carbon dioxide is based on a heterogeneous-homogeneous mechanism, wherein first the heterogeneous activation of methane with formation of different intermediates, such as $CH_3$, $CH_2$, CH, $H_2$, takes place, which intermediates then take part in radical reactions. Non-isothermal conditions of the reactor during the process allow to increase the benzene selectivity.

Non-isothermal conditions, namely a less temperature at the outlet of the reactor allows to decrease the possible benzene oxidation, decomposition and its polymerization and condensation. The starting gas flow may be preheated up to the reaction temperature prior entering the reactor.

The process according to the present invention allows to realize an in situ regeneration of a part of coke fragments with carbon dioxide and also allows to produce active coke fragments (H containing).

A preferred first catalytic material used in the process is $Mn(NO_3)_2$, which increases the benzene yield. Manganese oxide, formed from $Mn(NO_3)_2$ on the reactor wall significantly decreases accumulation of coke fragments during the process.

Further advantages and features of the process of the present invention will now become apparent by the following detailed examples.

EXAMPLE 1

A process according to the present invention was carried out in a reactor having a diameter of 10 mm, the reactor inner walls were treated with 2 ml of $Mn(NO_3)_2$ catalyst. A mixture of 50 mol-% methane and 50 mol-% carbon dioxide was introduced into the reactor at a temperature of 965° C. The reactor was non-isothermal and had a temperature profile of 965° C. at the inlet side and of 715° C. at the outlet side of the gas flow. The pressure in the reactor was 2 bar.

The following table 1 illustrates the products obtained and their contents in the product gas flow obtained from the reactor. All data shown in the following tables are given in mol-%.

TABLE 1

| | |
|---|---|
| Hydrogen | 24.48 |
| Methane | 23.84 |
| Ethylene | 0.73 |
| Carbonmonoxide | 12.57 |
| Carbondioxide | 37.10 |
| Benzene | 0.75 |
| Ethane | 0.06 |
| Toluene | 0.025 |
| Water | 0.45 |

The methane conversion was 38 mol-%, the benzene selectivity was 32.1 mol-%, the benzene yield was 12.2 mol-% and the coke selectivity was 15.2 mol-%.

EXAMPLE 2

This example was carried out-like example 1, but with a starting gas flow having 40 mol-% methane and 60 mol-% carbon dioxide and additionally 2 ml catalyst (2-20%) $W—Mn_3O_4/(2-20\%)$ $Sr—La_2O_3$ on the top of the reactor.

The results of example 2 are given in table 2.

TABLE 2

| | |
|---|---|
| Hydrogen | 22.1 |
| Methane | 18.1 |
| Ethylene | 0.26 |
| Carbonmonoxide | 26.64 |
| Carbondioxide | 32.44 |
| Benzene | 0.38 |
| Ethane | 0.06 |
| Toluene | 0.02 |

The methane conversion was 39.6 mol-%, the benzene selectivity was 19.2 mol-%, the benzene yield was 7.7 mol-%, and the coke selectivity was 10.7 mol-%.

EXAMPLE 3

Example 3 was carried out like example 1, but with a reaction mixture as starting gas flow having 70 mol-% methane and 30 mol-% carbon dioxide.

The results of example 3 are given in table 3.

TABLE 3

| | |
|---|---|
| Hydrogen | 35.72 |
| Methane | 36.7 |
| Ethylene | 0.99 |
| Carbonmonoxide | 6.04 |
| Carbondioxide | 19.30 |
| Benzene | 1.1 |

TABLE 3-continued

| | |
|---|---|
| Ethane | 0.11 |
| Toluene | 0.04 |

The methane conversion was 35.8. mol-%, the benzene selectivity was 32.2 mol-%, the benzene yield was 11.53 mol-%, and the coke selectivity was 43.5 mol-%.

EXAMPLE 4

This example was carried out using the conditions as in example 3, but the maximum temperature of the reaction was 940° C. at the inlet of the reactor.

The results of example 4 are given in table 4.

TABLE 4

| | |
|---|---|
| Hydrogen | 22.90 |
| Methane | 47.90 |
| Ethylene | 1.20 |
| Carbonmonoxide | 2.57 |
| Carbondioxide | 24.54 |
| Benzene | 0.78 |
| Ethane | 0.09 |
| Toluene | 0.02 |

The methane conversion was 22.0 mol-%, the benzene selectivity was 36.0 mol-%, the benzene yield was 8.0 mol-%, and the coke selectivity was 40.2 mol-%.

EXAMPLE 5

The reaction of example 5 was carried out using the conditions as outlined in example 1, but using a reactor with an internal diameter of 25 mm. The pressure in the reactor was 2 bar.

The results are given in table 5.

TABLE 5

| | |
|---|---|
| Hydrogen | 21.56 |
| Methane | 27.80 |
| Ethylene | 0.81 |
| Carbonmonoxide | 8.60 |
| Carbondioxide | 40.21 |
| Benzene | 0.94 |
| Ethane | 0.06 |
| Toluene | 0.02 |

The methane conversion was 32.0 mol-%, the benzene selectivity was 41.5 mol-%, the benzene yield was 13.3 mol-%, and the coke selectivity was 13.7 mol-%.

EXAMPLE 6

The process of example 6 was carried out using the same conditions as in example 1, but without using a catalyst.

The results are given in table 6.

TABLE 6

| | |
|---|---|
| Hydrogen | 19.35 |
| Methane | 31.0 |
| Ethylene | 1.05 |
| Carbonmonoxide | 5.10 |
| Carbondioxide | 42.50 |
| Benzene | 0.82 |
| Ethane | 0.05 |
| Toluene | 0.02 |

The methane conversion was 28.0 mol-%, the benzene selectivity was 40.6 mol-%, the benzene yield was 12.96 mol-%, and the coke selectivity was 18.7 mol-%.

EXAMPLE 7

The process of example 7 was carried out using the same conditions as in example 6, but using a reaction mixture of 70 mol-% methane and 30 mol-% carbon dioxide.
The results are given in table 7.

TABLE 7

| | |
|---|---|
| Hydrogen | 35.72 |
| Methane | 36.7 |
| Ethylene | 0.99 |
| Carbonmonoxide | 6.04 |
| Carbondioxide | 19.31 |
| Benzene | 1.1 |
| Ethane | 0.11 |
| Toluene | 0.04 |

The methane conversion was 35.8 mol-%, the benzene selectivity was 32.2 mol-%, the benzene yield was 11.53 mol-%, and the coke selectivity was 43.5 mol-%.

EXAMPLE 8

The process of example 8 was carried out using the same conditions as in example 6, but using a reaction mixture of 50 mol-% $CH_4$, 40 mol-% $CO_2$ and 10 mol-% air without using a catalyst.
The results are given in table 8.

TABLE 8

| | |
|---|---|
| Hydrogen | 18.84 |
| Methane | 32.90 |
| Ethylene | 0.88 |
| Carbonmonoxide | 5.32 |
| Carbondioxide | 37.08 |
| Benzene | 0.76 |
| Ethane | 0.07 |
| Toluene | 0.02 |
| Nitrogen | 4.13 |

The methane conversion was 25.8 mol-%, the benzene selectivity was 39.8 mol-%, the benzene yield was 10.3 mol-% and the coke selectivity was 44.75 mol-%.

EXAMPLE 9

The process of example 9 was carried out using the same conditions as in example 3, but using a reactor having an inner diameter of 4 mm.
The results are given in Table 9

TABLE 9

| | |
|---|---|
| Hydrogen | 2.65 |
| Methane | 65.78 |
| Ethylene | 1.51 |
| Carbonmonoxide | 1.71 |
| Carbondioxide | 27.62 |
| Benzene | 0.22 |
| Ethane | 0.47 |
| Toluene | 0.022 |

The methane conversion was 10 mol-%, the benzene selectivity was 20 mol-%, the benzene yield was 2 mol-% and the coke selectivity was 19.8 mol-%.

The features disclosed in the foregoing description and in the claims may, both separately and in any combination thereof be material for realizing the invention in diverse forms thereof.

The invention claimed is:

1. A process for producing benzene, ethylene and synthesis gas, comprising the steps of:
    i) introducing a feed gas comprising methane and carbon dioxide in a molar ratio in the range from 40:60 to 70:30 into a reactor defined by at least one reactor wall;
    ii) oxidizing the feed gas in the reactor in the presence of a non-zeolite catalyst material consisting essentially of $Mn(NO_3)_2$; and
    iv) recovering a product comprising benzene, ethylene and synthesis gas from the reactor.

2. The process according to claim 1, wherein said reactor wall has an interior surface which is treated with said catalyst material.

3. The process according to claim 2, wherein said catalyst material, mixed with $SiO_2$ sol-gel.

4. The process according to claim 3, wherein a second oxidant comprising air or oxygen is mixed with the feed gas in the reactor during the oxidation of said feed gas.

5. The process according to claim 4, wherein the concentration of the second oxidant relative to the feed gas is not more than 2% by volume.

6. The process according to claim 2, wherein said reactor has a reactor inlet and a reactor outlet and wherein the feed gas oxidation is carried out at a temperature profile which is in the range of from about 1500° C. to about 1000° C. at the reactor inlet and from about 700° C. to about 600° C. at the reactor outlet.

7. The process according to claim 3, wherein the feed gas is introduced into the reactor at a temperature of about 965° C. and the product is recovered from the reactor at a temperature of about 715° C.

8. The process according to claim 1, wherein said reactor has a reactor inlet and a reactor outlet and wherein there is a second catalyst material comprised of a basic oxide in the reactor at the reactor inlet.

9. The process according to claim 8, wherein said second catalyst material comprises $WO_3$, SrO, $La_2O_3$, $MnO_2$, W—$Mn_3O_4$ or Sr—$La_2O_3$.

10. The process according to claim 8, wherein said second catalyst material comprises W—$Mn_3O_4$/Sr—$La_2O_3$.

11. The process according to claim 1, wherein the mole ratio of methane to carbon dioxide in the feed gas is about 50:50.

12. The process according to claim 1, wherein said reactor has a reactor inlet and a reactor outlet and wherein the feed gas oxidation is carried out at a temperature profile which is in the range of from about 1500° C. to about 1000° C. at the reactor inlet and from about 700° C. to about 600° C. at the reactor outlet.

13. The process according to claim 2, wherein said reactor has a reactor inlet and a reactor outlet and wherein the feed gas oxidation is carried out at a temperature profile which is in the range of from about 1500° C. to about 1000° C. at the reactor inlet and from about 700° C. to about 600° C. at the reactor outlet.

14. The process according to claim 4, wherein the feed gas is introduced into the reactor at a temperature of about 965° C. and the product is recovered from the reactor at a temperature of about 715° C.

15. The process according to claim 6, wherein said reactor has a reactor inlet and a reactor outlet and wherein there is a second catalyst material comprised of a basic oxide in the reactor at the reactor inlet.

16. The process according to claim 12, wherein said reactor has a reactor inlet and a reactor outlet and wherein there is a second catalyst material comprised of a basic oxide in the reactor at the reactor inlet.

17. The process according to claim 12, wherein said reactor has a reactor inlet and a reactor outlet and wherein there is a second catalyst material comprised of $W—Mn_3O_4/Sr—La_2O_3$ in the reactor at the reactor inlet.

18. The process according to claim 14, wherein said reactor has a rector inlet and a reactor outlet and wherein there is a second catalyst material comprised of $W—Mn_3O_4/Sr—La_2O_3$ in the reactor at the reactor inlet.

19. The process according to claim 2, wherein the mole ratio of methane to carbon dioxide in the feed gas is about 50:50.

20. The process according to claim 6, wherein the mole ratio of methane to carbon dioxide in the feed gas is about 50:50.

21. The process according to claim 7, wherein the mole ratio of methane to carbon dioxide in the feed gas is about 50:50.

22. The process according to claim 1, wherein the interior wall of the reactor is cylindrical and with an interior diameter of about 2 to 1000 mm.

23. The process according to claim 2, wherein the interior wall of the reactor is cylindrical with an interior diameter of about 2 to 1000 mm.

24. The process according to claim 6, wherein the interior wall of the reactor is cylindrical with an interior diameter of about 2 to 1000 mm.

25. The process according to claim 7, wherein the interior wall of the reactor is cylindrical with an interior diameter of about 2 to 1000 mm.

26. The process according to claim 22, wherein the reactor has a length and the length to diameter ratio of the reactor is from about 200 to 1 to about 100 to 50.

27. The process according to claim 23, wherein the reactor has a length and the length to diameter ratio of the reactor is from about 200 to 1 to about 100 to 50.

28. The process according to claim 24, wherein the reactor has a length and the length to diameter ratio of the reactor is from about 200 to 1 to about 100 to 50.

29. The process according to claim 25, wherein the reactor has a length and the length to diameter ratio of the reactor is from about 300 to 1 to about 100 to 50.

* * * * *